(12) United States Patent  
Luisi et al.

(10) Patent No.: US 8,103,088 B2
(45) Date of Patent: Jan. 24, 2012

(54) THREE-DIMENSIONAL IMAGE CAPTURE SYSTEM

(75) Inventors: Jerold N. Luisi, Phoenix, AZ (US); Timothy R. Littlefield, Phoenix, AZ (US); Jeanne K Pomatto-Hertz, Scottsdale, AZ (US)

(73) Assignee: Cranial Technologies, Inc., Tempe, AZ (US)

( * ) Notice: Subject to any disclaimer, the term of this patent is extended or adjusted under 35 U.S.C. 154(b) by 482 days.

(21) Appl. No.: 12/383,198

(22) Filed: Mar. 20, 2009

(65) Prior Publication Data

US 2010/0239135 A1 Sep. 23, 2010

(51) Int. Cl.
*G06K 9/00* (2006.01)
*H04N 13/02* (2006.01)

(52) U.S. Cl. .......................................... 382/154; 348/48
(58) Field of Classification Search ................. 382/154, 382/225; 348/47, 48
See application file for complete search history.

(56) References Cited

U.S. PATENT DOCUMENTS

| | | | | |
|---|---|---|---|---|
| 5,850,352 A | * | 12/1998 | Moezzi et al. | 345/419 |
| 6,977,651 B1 | * | 12/2005 | Matsumoto et al. | 345/419 |
| 7,127,101 B2 | * | 10/2006 | Littlefield et al. | 382/154 |
| 7,142,701 B2 | * | 11/2006 | Littlefield et al. | 382/128 |
| 7,177,461 B2 | * | 2/2007 | Littlefield et al. | 382/156 |
| 7,190,826 B2 | * | 3/2007 | Russell et al. | 382/154 |
| 7,242,798 B2 | * | 7/2007 | Littlefield et al. | 382/154 |
| 7,305,369 B2 | * | 12/2007 | Littlefield et al. | 706/16 |
| 7,333,113 B2 | * | 2/2008 | Gordon | 345/475 |
| 7,542,950 B2 | * | 6/2009 | Littlefield et al. | 706/16 |
| 7,978,378 B2 | * | 7/2011 | Pishdadian et al. | 358/474 |
| 2004/0197016 A1 | * | 10/2004 | Littlefield et al. | 382/128 |
| 2006/0034548 A1 | * | 2/2006 | Pishdadian et al. | 382/312 |
| 2007/0110299 A1 | * | 5/2007 | Littlefield et al. | 382/154 |
| 2007/0140549 A1 | * | 6/2007 | Littlefield et al. | 382/154 |
| 2009/0256800 A1 | * | 10/2009 | Kaufman | 345/156 |
| 2009/0316965 A1 | * | 12/2009 | Mailling et al. | 382/128 |
| 2010/0231692 A1 | * | 9/2010 | Perlman et al. | 348/48 |
| 2010/0238273 A1 | * | 9/2010 | Luisi et al. | 348/48 |
| 2010/0239135 A1 | * | 9/2010 | Luisi et al. | 382/128 |

* cited by examiner

*Primary Examiner* — John Lee
(74) *Attorney, Agent, or Firm* — Donald J. Lenkszus

(57) ABSTRACT

Apparatus to capture three-dimensional images of a head comprises a plurality of image capturing device modules, each module comprises a plurality of image-capturing devices; and a rigid support structure supporting the plurality of image capturing device modules to define a space wherein an image of the head may be disposed. The rigid support structure supports all of the modules in predetermined relationship to each other and to the space. The rigid support structure further supports the modules in positions such that each module is positioned to capture a group of first images of a corresponding surface portion of a head disposed within the space such that each group of first images captured by the corresponding module captures a substantially different surface portion of the head disposed within the space.

51 Claims, 11 Drawing Sheets

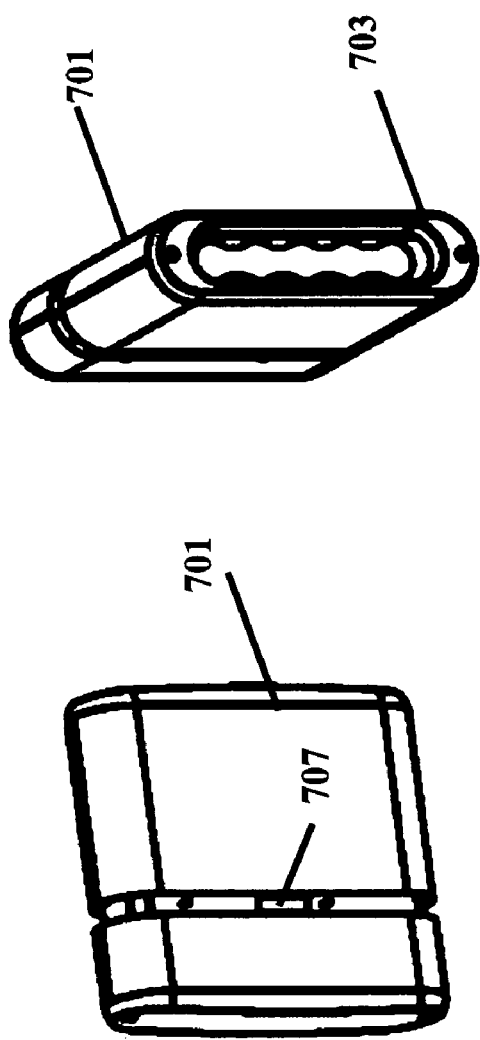

THREE-DIMENSIONAL IMAGE CAPTURE SYSTEM

This application is related to the following application and patents all assigned to Cranial Technologies, Inc. a common assignee with this application: Published patent application Ser. No. 11/471,965 which is a division of U.S. Pat. No. 7,305,369; Cranial Remodeling Device Database U.S. Pat. No. 7,177,461; Automatic Selection of Cranial Remodeling Device Configuration, U.S. Pat. No. 7,242,798; Automatic Selection of Cranial Remodeling Device Trim Lines, U.S. Pat. No. 7,127,101; and Cranial Remodeling Device Manufacturing System, U.S. Pat. No. 7,142,701. The teachings and disclosures of the above-identified application and patents are incorporated herein.

FIELD OF THE INVENTION

This invention pertains to imaging systems, in general, and to a three-dimensional imaging system for capturing three-dimensional images of the totality of surface of an object that is not constrained from moving, in particular

BACKGROUND OF THE INVENTION

Treatment of infants with deformational plagiocephaly with cranial remodeling bands has become a standard of care in the United States. Cranial Technologies, Inc the assignee of the present invention pioneered this treatment.

Cranial Technologies, Inc. has further carried forward with its pioneering efforts by the development of an image capturing system that captures three-dimensional images of the entirety of the surface of an object, in general, and the entirety of the surface of a subject's head, in particular. The Cranial Technologies, Inc. image capturing system is described in the above-identified patents and application.

Cranial Technologies, Inc. recognized that any imaging system to be used in a clinical setting had to be robust, easy to use, and easy to calibrate and maintain without the need for hiring additional technical staff to run the equipment. Image acquisition, processing, and viewing of the data had to be performed in substantially real time in order to ensure that no data was missing before allowing the patient to leave the office.

The Cranial Technologies, Inc. image capturing system captures accurate three-dimensional images of objects and is configured such that the object having its image captured does not have to be stationary or fixed in one particular orientation. The Cranial Technologies system captures a three-dimensional digitized image of the entirety of the surface of an object even though the object may move in a generally non-predetermined manner within a predetermined space. A sequence of instantaneous three-dimensional images may be captured to provide a movie of the object as it moves.

The Cranial Technologies, Inc. system utilizes a plurality of image capturing device groups. Each group comprises a plurality of image capturing devices arranged as a module. The image capturing devices define a space wherein an object may be disposed. The object is movable within the space. The image capturing device groups are positioned such that: each group is positioned to capture a group of first images of a corresponding surface portion of the object. Each group of first images captures a substantially different surface portion of the object disposed within the space.

In one embodiment of the Cranial Technologies, Inc. system each group includes digital cameras and a projector that projects random infrared patterns onto the object to instantaneously capture a 360° full surface image of the object. The image is acquired in 0.008 seconds and processed for viewing in software. The data acquired is viewable on a display or printed out as a point cloud, wire frame, or surface, on which a digital photograph (i.e. texture) is automatically overlaid. A texture overlay of the object may be provided. The use of a texture overlay permits advantageous visual confirmation of the object, or in the case of a subject, the identity of the subject.

The Cranial Technologies, Inc. system comprises a plurality of groups of hardware that is supported on tripod structures that are individually positioned and adjusted to predetermined positions relative to each other.

Although the Cranial Technologies, Inc. system is highly effective, it is desirable to provide a structure for the system that requires ensures accurate and consistent imaging from installation to installation by providing physically consistent placement of the imaging devices and further does not require periodic physical adjustment to maintain the placement.

SUMMARY OF THE INVENTION

In accordance with an aspect of an embodiment, apparatus to capture three-dimensional images of a head is provided. The apparatus comprises a plurality of image capturing device groups, each group comprises a plurality of image-capturing devices. A single support structure supports the plurality of image capturing device groups in predetermined relationship to each other. The predetermined relationship defines a space. The support structure supports the plurality of image capturing device groups in positions such that each group is positioned to capture a group of first images of a corresponding surface portion of a head disposed within the space. Each group of first images captured by the corresponding image capturing device groups captures a substantially different surface portion of the head disposed within the space. Each group is disposed on the structure such that the totality of the surface of the head within the space is captured.

In accordance with yet a further aspect of the embodiment, the support structure comprises low-reflectivity surfaces.

Further in accordance with an embodiment of the invention, apparatus to capture three-dimensional images of a head comprises a plurality of image capturing device modules, each module comprises a plurality of image-capturing devices. The apparatus further comprises a rigid support structure rigidly supporting each of the modules in predetermined relationship to each other such that one module is disposed in a first plane centered on an axis and the remaining modules are disposed in a second plane parallel to the first plane and centered on the axis. The head is disposed in a predetermined position with respect to the axis and the second plane.

In accordance with an aspect of the embodiment, apparatus to capture three-dimensional images of a head comprises a plurality of image capturing device modules, each module comprises a plurality of image-capturing devices. The apparatus comprises a rigid support structure rigidly supporting each of the image capturing device modules in predetermined relationship to each other such that one module is disposed in a first horizontal plane centered on a vertical axis and the remaining modules are disposed along the circumference of a circle in a second plane parallel to the first plane and centered on the vertical axis. The head is disposed in a predetermined position with respect to the vertical axis and the second plane. The rigid support structure comprises first, second and third vertical supports. The first, second and third vertical supports are spaced along the circumference such that the first and second supports are spaced apart by the same circumferential distance as the second and third supports. The rigid support structure comprises first, second, third and fourth arcuate support members. The first arcuate support member is rigidly coupled to the first vertical support. The second arcuate support member is rigidly coupled to the first and said second vertical supports. The third arcuate support member is rigidly coupled to the second and third vertical supports. The fourth arcuate support member is rigidly coupled to the third vertical support. The remaining modules comprise a first module supported on the first arcuate member, a second module supported on the second arcuate member; a third module supported on the third arcuate member; and a fourth module supported on the fourth arcuate member.

In accordance with yet an even further embodiment, apparatus is provided to capture three-dimensional images of a head. The apparatus comprises a plurality of image capturing modules. Each module comprises a plurality of image-capturing devices. A single support structure supports the plurality of image capturing modules in predetermined relationship to each other. The predetermined relationship defines a space. The support structure supports the plurality of image capturing modules in positions such that each module is positioned to capture a group of first images of a corresponding surface portion of a head disposed within the defined space. Each group of first images captures a substantially different surface portion of the head. Each module is disposed on the structure such that first images capture the totality of the surface of the head.

In accordance with an aspect of the embodiment the apparatus for capturing three-dimensional images of a head comprises a plurality of image capturing device modules; each module comprising a plurality of image-capturing devices; and a support structure supporting the image capturing device modules in predetermined relationship to each other such that at least one module is disposed in a first plane centered on an axis and other modules are disposed in a second plane parallel to the first plane and centered on the axis. The apparatus automatically operates the plurality of image capturing device modules when the head is disposed in a predetermined position with respect to the axis and the second plane.

In one embodiment the said automatically operating apparatus comprises sensing apparatus to sense the position of the head.

In accordance with a further aspect of the embodiment the automatically operating apparatus comprises apparatus to automatically position the subject to the predetermined position.

In accordance with another aspect of the embodiment the displacing apparatus comprises a vertically displaceable apparatus and the vertically displaceable apparatus is electrically actuatable.

BRIEF DESCRIPTION OF THE DRAWING

The invention will be better understood from a reading of the following detailed description of embodiments of the invention taken in conjunction with the drawing figures in which like reference designators are used to identify like elements, and in which:

FIG. 7 is a right side view of a module portion of the image capture system of FIG. 1;

FIG. 8 is a front of a module portion of the image capture system of FIG. 1;

FIG. 9 is a left side view of a module portion of the image capture system of FIG. 1;

FIG. 10 is a rear view of a module portion of the image capture system of FIG. 1;

DETAILED DESCRIPTION

Figure 1:
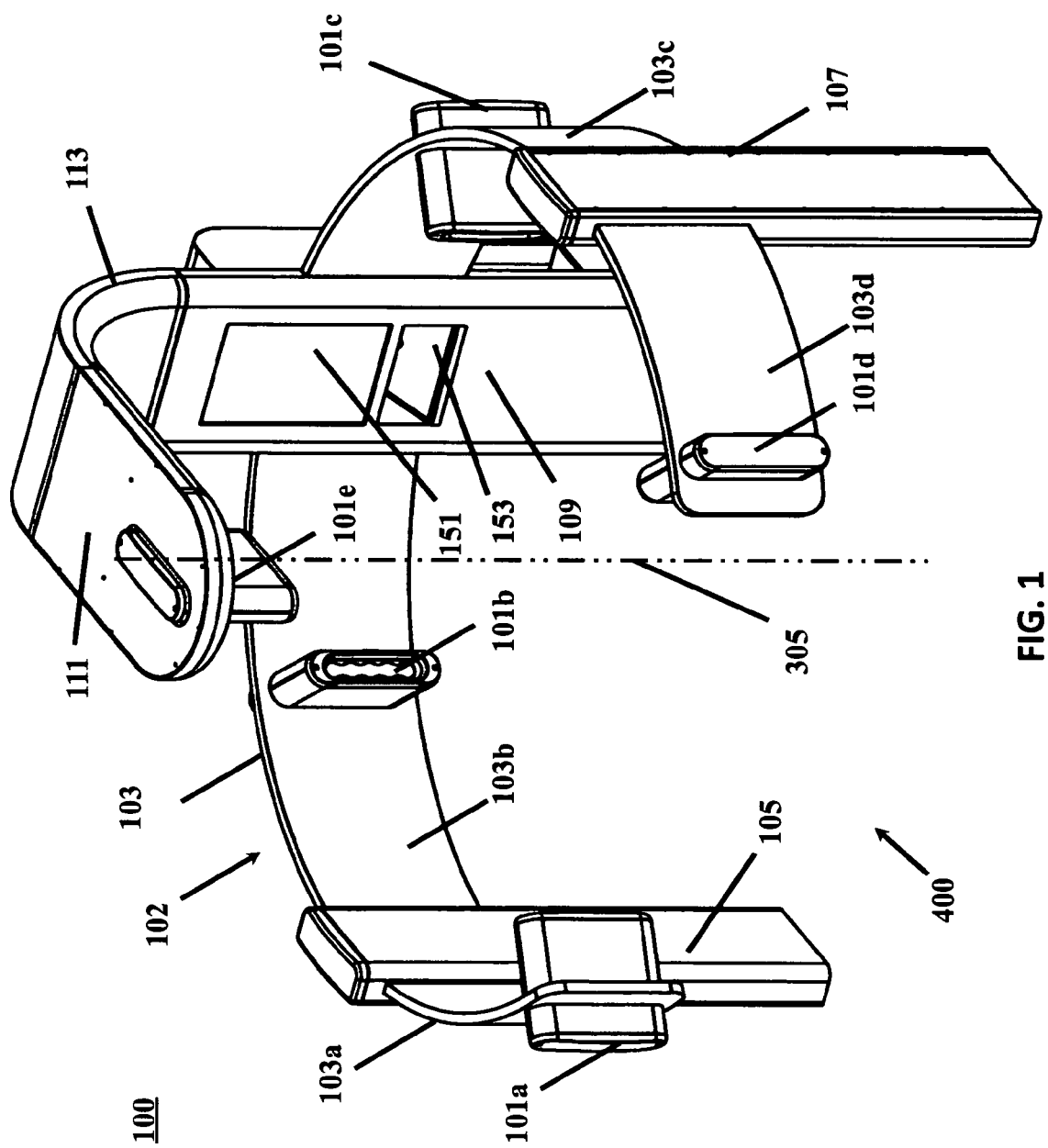
FIG. 1 is an isometric view of an image capture system in accordance with the invention.
Figure 2:
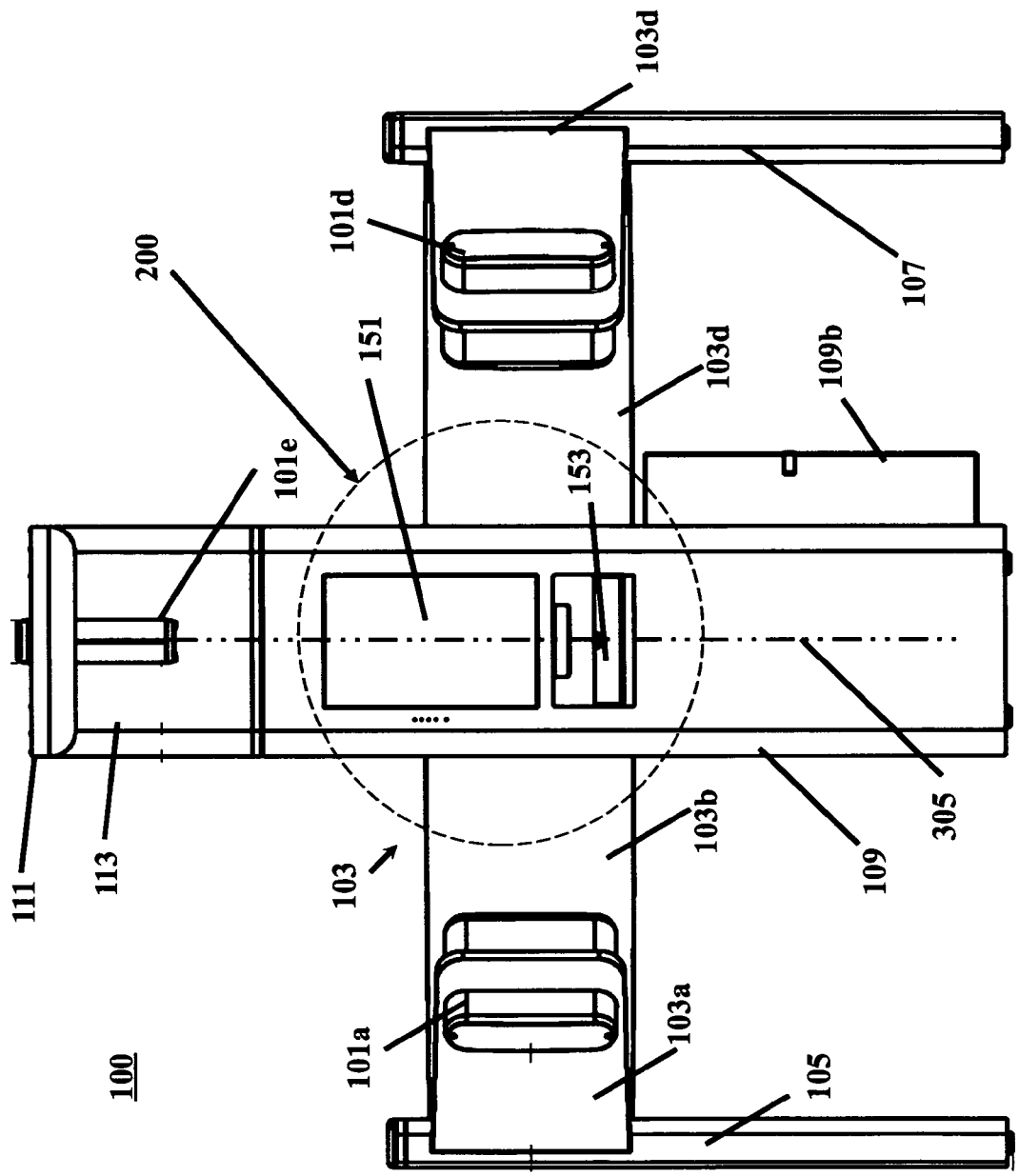
FIG. 2 is a front planar view of a portion of the image capture system of FIG. 1.

The present invention has advantages over prior system arrangements. One significant advantage is that all the cameras and projectors are disposed in a fixed geometric relationship to each other. A significant benefit resulting from the fixed relationship is that each system installation does not require extensive camera set-up positioning which in turn provides for consistent and standardized system installations.

The structural configuration of the embodiment provides a feeling of openness to users of the system which is advantageous. Prior systems utilizing tripod supports for cameras were perceived as constraining. The structural configuration of the embodiment provides a more open volume with more room to permit subjects and system operators or clinicians ingress and egress into and out of the structure.

The embodiment provides the further advantage that all cabling between the image capturing devices, projectors and other apparatus are contained within the structure. Providing the cabling within the structure also adds to the feeling of openness and also protects the system from inadvertent interaction with the cabling.

An additional advantage of the embodiment is that the system structure is fabricated from rolled welded steel sections that provide a rigid heavy structure. The structural mass and the mounting of the structure to the floor provides significant vibration isolation that improves the quality of the images.

One further advantage of the embodiment that has been observed is that room produced optical noise such as stray reflections are noticeably reduced providing images with better contrast and less stray data over prior systems.

The various embodiments of the invention may be utilized to obtain three-dimensional surface images of the entirety of an object which may be a subject's head or a subject's whole body or other objects.

In addition, the embodiments of the invention include an integrated display. One advantageous use of the display is as an attention attractor for children when the system is utilized to capture images of an infant or child. For example, videos may be displayed to help keep an infant's or child's attention and focus directed on the display.

One embodiment of the invention includes an automated stool like apparatus that utilizes a foot switch to adjust the height of the stool. In the past, a manual stool was used that required simultaneously holding a child and adjusting stool height.

FIGS. 1 through 6 show one embodiment of an image capture system 100. System 100 includes a plurality of groups of image capturing apparatus 101a, 101b, 101c, 101d, 101e all supported on a support apparatus 102. Each group of image capturing apparatus 101a, 101b, 101c, 101d, 101e is operable such that a three dimensional image is captured for a surface portion of an object that is disposed within the field of view of the groups. The images from all groups 101a, 101b, 101c, 101d, 101e are combined to produce an image of the entirety of the surface of the object.

In system 100, each group of image capturing apparatus 101a, 101b, 101c, 101d, 101e includes a plurality of digital cameras and a projector. Neither the cameras not the projectors are shown in the drawing figures. Each camera may be any commercially available digital camera such as, for example, a CCD camera, which is a high-resolution type camera that is commercially available. Each projector in a group projects a pattern onto the object to facilitate processing of the images captured by the corresponding plurality of digital cameras in the same group into a three-dimensional image of a corresponding portion of the object. Each projector projects a random infrared pattern onto the object that permits an algorithm described in the Cranial Technologies, Inc. patents and patent application identified hereinabove to easily utilize triangulation to generate a digitized three-dimensional representation of the corresponding portion of the object. The cameras in each group 101a, 101b, 101c, 101d, 101e are positioned to provide images that are utilized by the algorithm.

By arranging a plurality of such groups 101a, 101b, 101c, 101d, 101e in a plurality of planes 301, 303, three-dimensional image portions are obtained that can be compiled to produce three-dimensional images of the entirety of an object.

Producing three-dimensional images of some objects are particularly difficult because such objects do not remain motionless. Furthermore the motion that some objects take is somewhat unpredictable. The object may have translational, rotational and angular motions simultaneously. The motions may be smooth or they may be jerky. The object may have translational movement in one direction while rotating in the opposite direction. The system of the invention is arranged to operate at a speed to capture the entirety of an object in stop-action in one single instant.

As noted herein above, a particularly useful application of the system of the invention is for use in capturing highly accurate three-dimensional images of the totality of the surface of the head of a subject. System 100 utilizes a safe and non-invasive method of obtaining a 3D model of the entirety of a subject's head. System 100 does not require the subject to be restrained in a specific orientation and captures a 360° surface image, which includes at least the face, top of the head, and lower occiput/neck region. A photographic image of the subject is acquired and can be seamlessly overlaid on the three-dimensional display of the head to guarantee patient identification. The digital model is processed and visualized within minutes to ensure that no data are missing before allowing the patient to leave the office. Operation of the system is simple, fast, and robust.

In operation, the cameras and projectors of all groups of image capturing apparatus 101a, 101b, 101c, 101d, 101e are simultaneously operated to capture digitized first images of corresponding surface portions of the object or subject's head.

The plurality of groups of image capturing apparatus 101a, 101b, 101c, 101d, 101e are supported by a support apparatus or structure 102 to define a space 200 within which a three-dimensional image is captured of the entirety of the object or a subject's head that is not shown. Although the illustrative embodiments shows a particular shaped spaces 200, it will be understood by those skilled in the art that the defined spaces 200 are only illustrative and the actual defined space may be of a different configuration. In other implementations, support structure 102 may support the image capturing apparatus to, for example, define a space 200 that is elongated in one or more directions.

Support structure 102 supports all of groups of image capturing apparatus 101a, 101b, 101c, 101d, 101e in predetermined relationship to each other and to the space 200. Support structure 102 further supports groups of image capturing apparatus 101a, 101b, 101c, 101d, 101e in positions such that each module 101a, 101b, 101c, 101d, 101e is positioned to capture a group of first images of a corresponding surface portion of a subject head or object disposed within space 200 such that each group of first images captured by the corresponding group of image capturing apparatus 101a, 101b, 101c, 101d, 101e captures a substantially different surface portion of a subject head or object disposed within space 200.

Support structure 102 comprises a first rigid arcuate structure 103 carrying a first portion of said groups of image capturing apparatus 101a, 101b, 101c, 101d in a first predetermined spatial relationship. Arcuate structure 103 supports each of groups of image capturing apparatus 101a, 101b, 101c, 101d in a predetermined or vertical alignment to a first or one horizontal plane 301.

A plurality of vertical support structures 105, 107, 109 are provided to support arcuate structure 103 at a predetermined uniform height. At least one vertical support structure 109 extends above arcuate structure 103 and supports a second rigid structure portion 111 substantially disposed in a second or other horizontal plane 303 having a predetermined parallel relationship to the first plane 301. The second rigid structure portion 111 supports a second portion of the plurality of groups of image capturing apparatus, i.e., group 101e in a predetermined fixed relationship above the first portion of the groups of image capturing apparatus 101a, 101b, 101c, 101d.

Arcuate support structure 103 comprising a plurality of arcuate support members 103a, 103b, 103c, 103d rigidly coupled to each other. Each arcuate support elements 103a, 103b, 103c, 103d supports a corresponding one group of image capturing apparatus 101a, 101b, 101c, 101d. The plurality of arcuate support elements 103a, 103b, 103c, 103d are supported by a plurality of vertical support structures 105, 107, 109.

Support structure 102 rigidly supports each of the groups of image capturing apparatus 101a, 101b, 101c, 101d, 101e in predetermined relationship to each other such that one group 101e is disposed in a horizontal plane 303 centered on a vertical axis 305 and the remaining groups 101a, 101b, 101c, 101d are disposed along the circumference of a circle 403 in a plane 301 parallel centered on the vertical axis 305. The subject head or object is desirably disposed in a predetermined position with respect to the vertical axis 305 and plane 301.

Each group of image capturing apparatus 101a, 101b, 101c, 101d is arranged in a corresponding module, and each of the modules 101a, 101b, 101c, 101d is disposed along the circumference of circle 403 and is spaced equidistant from each adjacent module.

Figure 3:
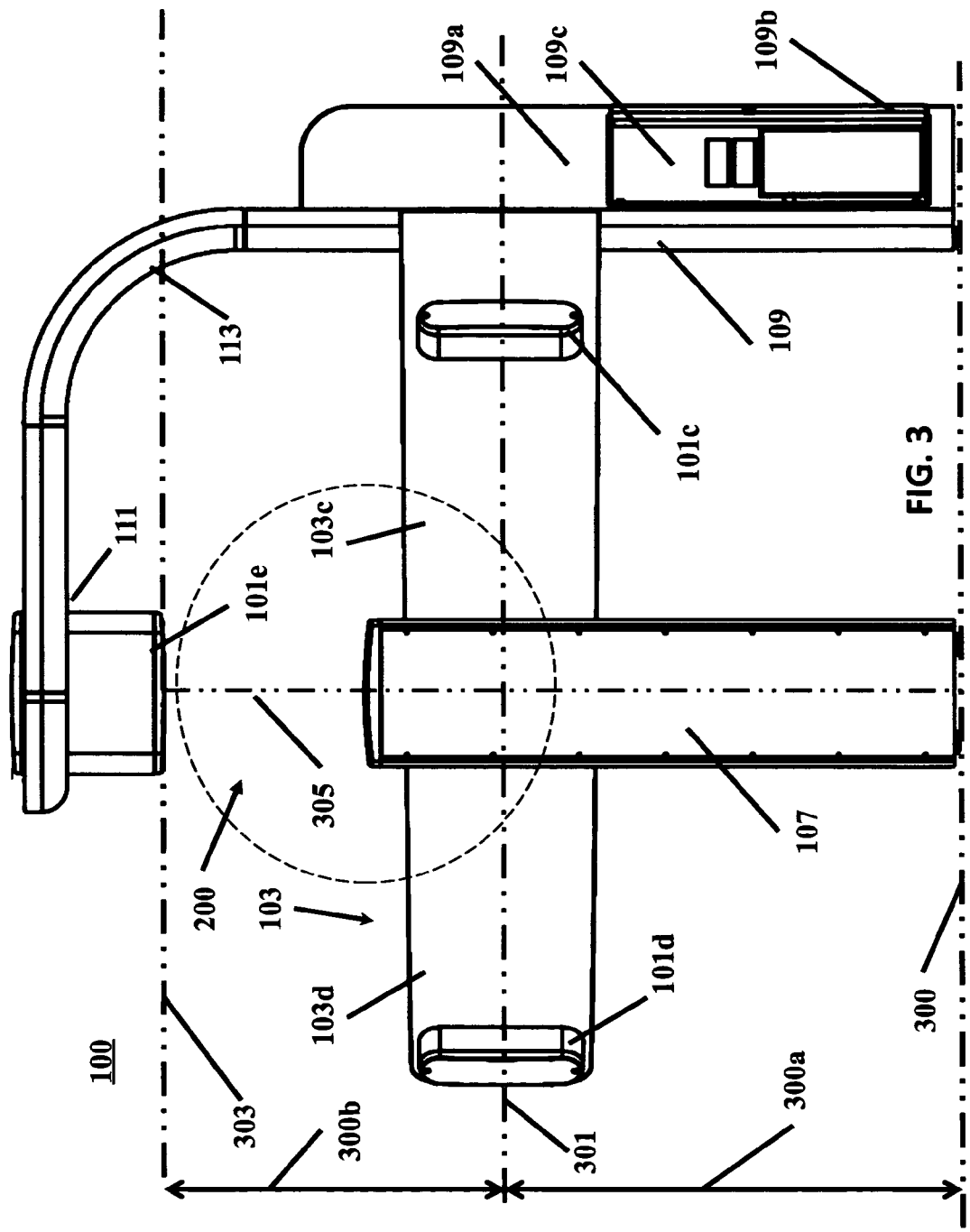
FIG. 3 is a right side planar view of the image capture system portion of FIG. 1.
Figure 4:
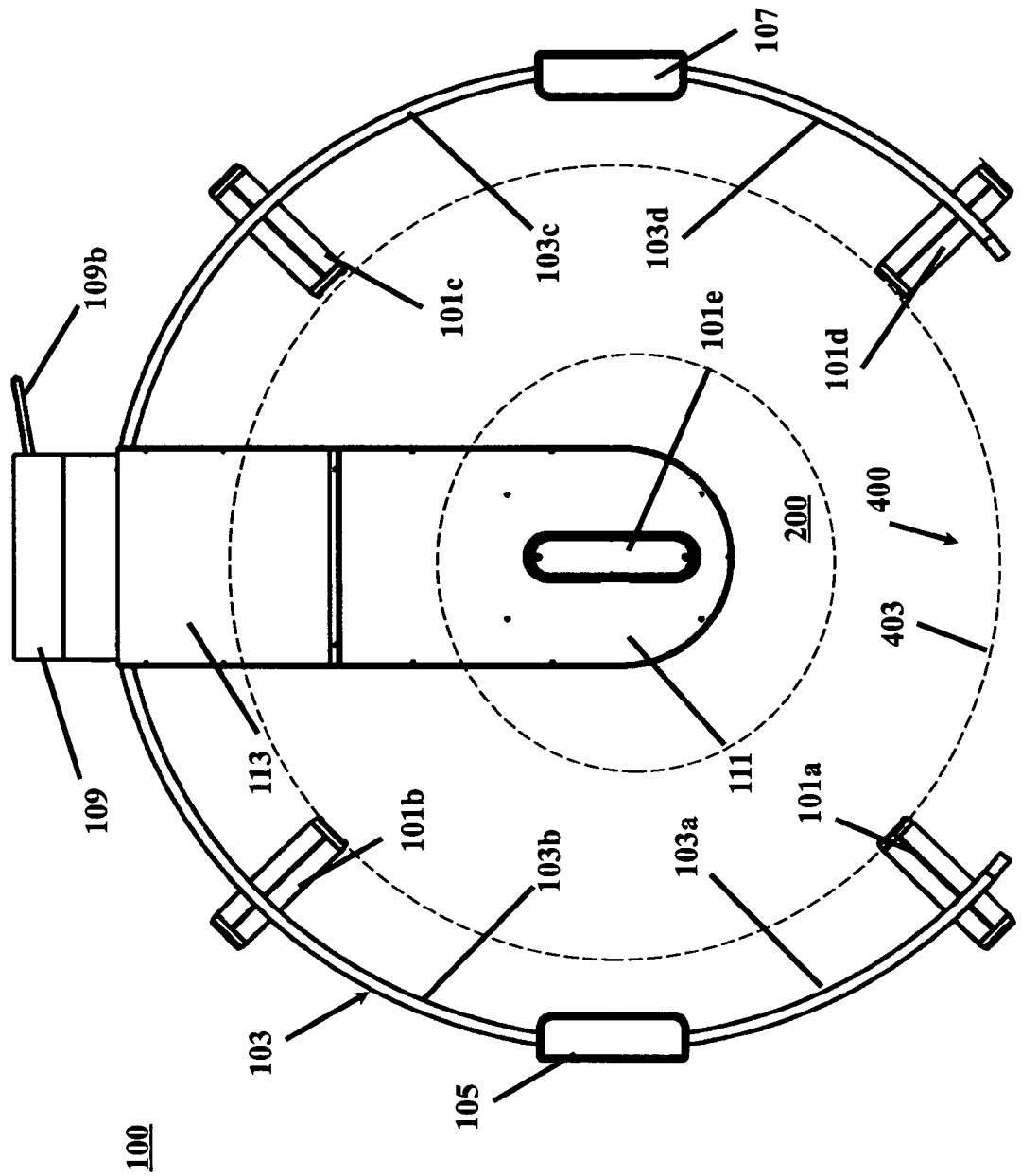
FIG. 4 is a top planar view of the image capture system portion of FIG. 1.
Figure 5:
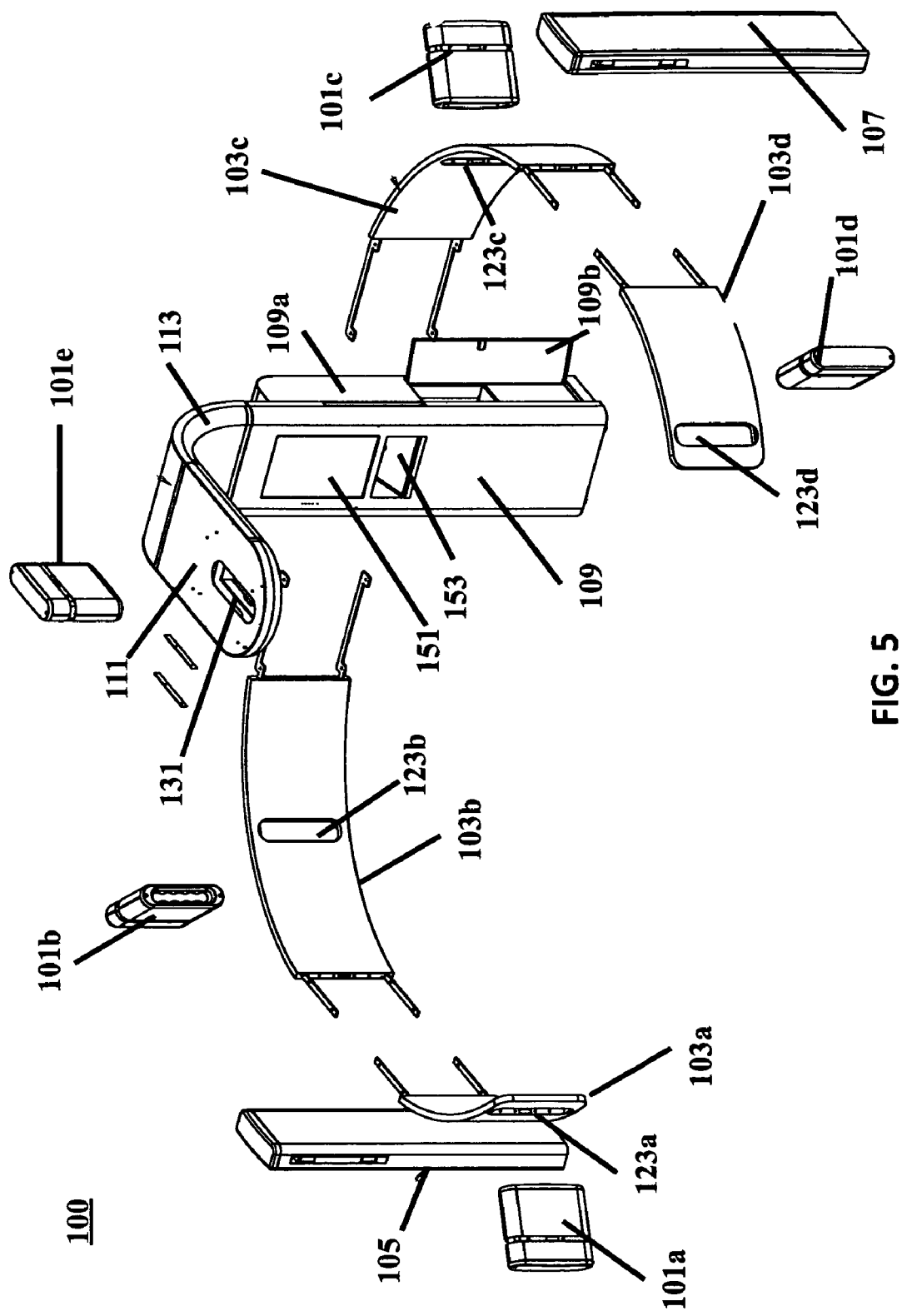
FIG. 5 is an exploded view the image capture system portion of FIG. 1.

Horizontal plane 303 is disposed a first predetermined distance 303b above horizontal plane 301 and horizontal plane 301 is disposed a second predetermined distance 303a above a base plane or floor 300 as shown in FIG. 3.

Yet further, the rigid support apparatus or structure 102 comprises an opening 400 for ingress and egress to positioning apparatus 601.

Turning back to FIG. 5, the various elements of system 100 are shown in exploded view. Support structure 102 comprises a first vertical support 105, a second vertical support 107, and a third vertical support 109 spaced apart about the circumference of circle 403 such that the first and third vertical supports 105, 109 are spaced apart by the same circumferential distance as the second and third vertical supports 107, 109. Rigid support structure 102 comprises first, second, third and fourth arcuate support members 103a, 103b, 103c, 103d. First arcuate support member 103a is rigidly coupled to first vertical support 105. Second arcuate support member 103b is rigidly coupled to the first vertical support 105 and third vertical support 109. Third arcuate support member 103c is rigidly coupled to second vertical support 107 and third vertical support 109. Fourth arcuate support member 103d is rigidly coupled to second vertical support 107.

First arcuate member 103a includes aperture 123a for receiving module 101a. Second arcuate member 103b includes aperture 123b for receiving module 101b. Third arcuate member 103c includes aperture 123c for receiving module 101c. Fourth arcuate member 103d includes aperture 123d for receiving module 101d.

First and fourth arcuate members 103a, 103d each have an unsupported end spaced apart from each other to provide opening 400 in structure 102 for ingress and egress. First and fourth arcuate members 103a, 103d are cantilevered from respective first and second vertical supports 105, 107.

Each arcuate support member 103a, 103b, 103c, 103d is connected to its respective vertical support or supports and to the adjacent arcuate member by means of connector brackets that are show extending from the ends of the arcuate members.

Second vertical support 109 extends above the second and third arcuate members 103b, 103c and is rigidly coupled to a horizontal member 111 which supports module 101e second vertical support 109 comprises an arcuate portion 113 rigidly coupled to horizontal member 111. Horizontal member 111 includes an aperture 131 for receiving module 101e.

Figure 6:
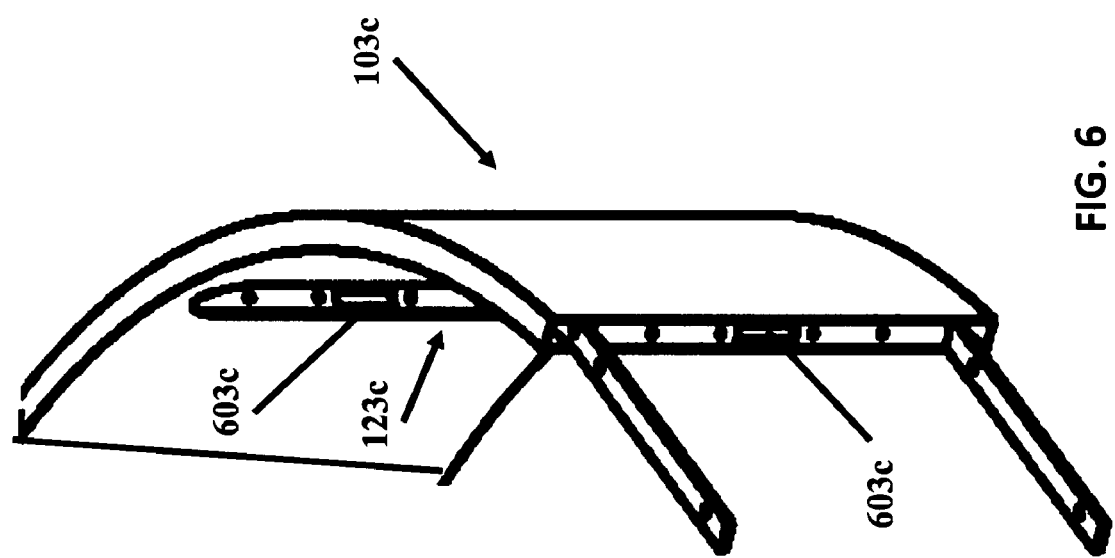
FIG. 6 is an enlarged view of a portion of FIG. 1

All cabling to modules 101a, 101b, 101c, 101d, 101e is carried in conduits or cable races extending through the structure 102. Each arcuate support member 103a, 103b, 103c, 103d includes an integral cable raceway. FIG. 6 shows a portion of a representative arcuate support member 103c having integral cable raceway 603c. It will be understood by those skilled in the art that each of arcuate support members 103a, 103b, 103c, 103d as well as members 111 and 113 include such cable raceways. Cables connecting the various modules 101a, 101b, 101c, 101d, 101e are carried in the cable raceways to the third vertical support 109 which includes a display 151, a keyboard or other input device or devices 153 and support electronics contained within portions 109a of vertical support 109 and accessible via an access door or opening 109b.

FIGS. 7 through 10 illustrate a representative one of the modules 101a, 101b, 101c, 101d, 101e. Each module 101a, 101b, 101c, 101d comprises a housing 701 that contains the corresponding plurality of image capturing devices, and projectors. Each housing 701 includes a front cover 703 and a rear cover 705. Front cover 703 as well as rear cover 705 is removable to permit adjustment of the plurality of image capturing devices and projector contained therein. Housing 701 includes apertures 707, 709 that match up with corresponding cable raceways in support structure 102.

Figure 11:
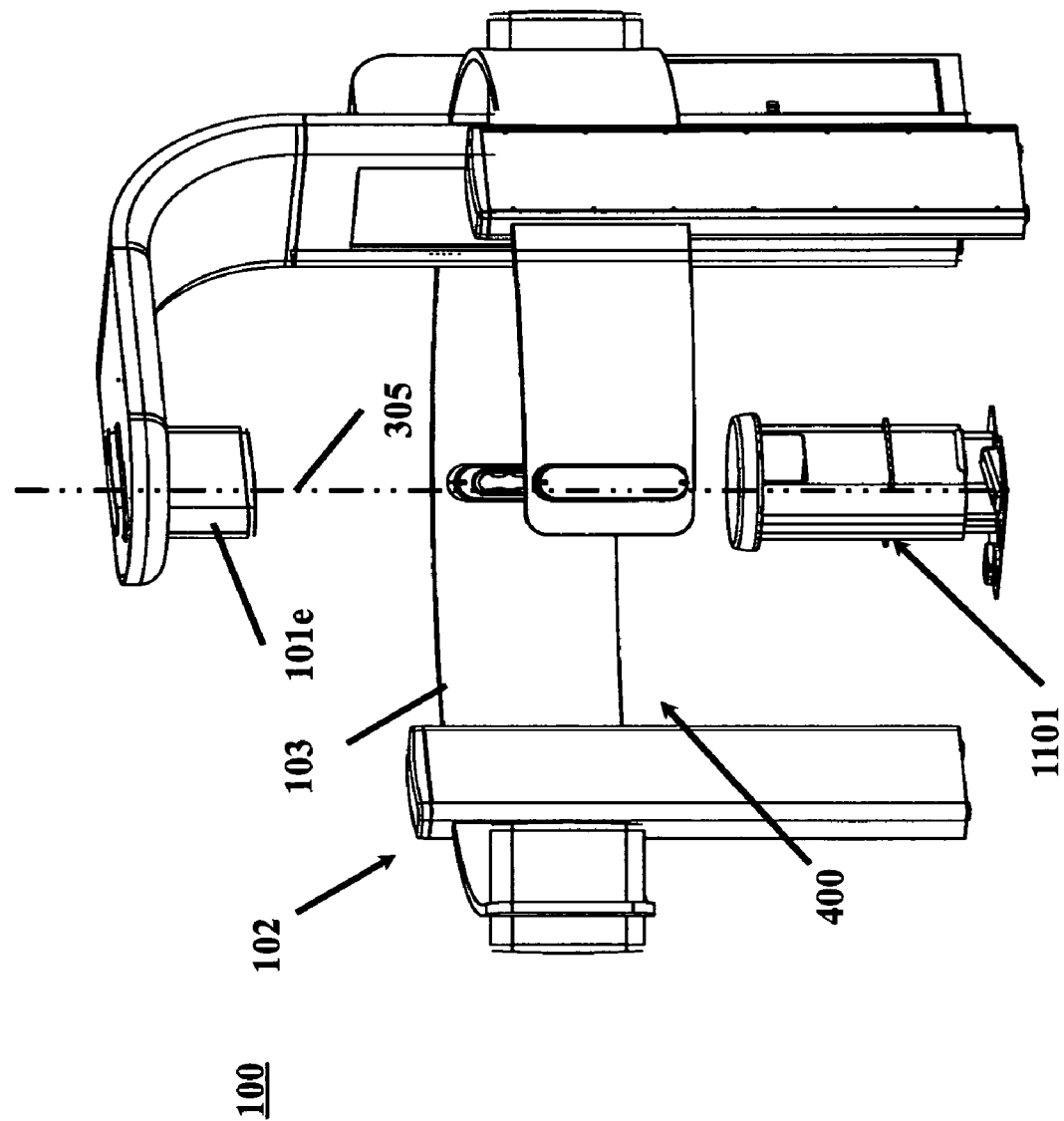
FIG. 11 is a perspective view of the image capture system of FIG. 1 showing a patient stool disposed therewith.

Turning now to FIG. 11, a positioning apparatus 1101 is disposed within the area and spatial volume defined by rigid support structure 102. Positioning apparatus 1101 is disposed in alignment with axis 305. Positioning apparatus 1101 comprises a vertically displaceable stool upon which the subject is seated. Positioning apparatus 1101 is vertically displaceable by the operator or clinician to adjust the position of the object or subject relative to groups of image capturing apparatus 101a, 101b, 101c, 101d, 101e. Advantageously, positioning apparatus 1101 includes foot operable actuators to control raising and lowering of positioning apparatus 1101. With this arrangement, the operator or clinician can adjust the height of the subject to a desirable position while, for example, in the instance where the subject is an infant. Positioning apparatus 1101 is utilized to adjust the initial position of the subject vertically relative to support structure 102.

It will be appreciated by those skilled in the art that other apparatus may be utilized to adjust the position of the subject or an object relative support structure 102. For example, the positioning of the subject or object may occur automatically. Reference points or areas on the subject or object may be identified and or detected by various sensors or detectors incorporated into system 100 and support structure 102. System 100 may automatically operate positioning apparatus 1101 to move or place the subject or object to a desired position or elevation. One such arrangement may utilize a sensing arrangement that identifies the eyes or irises of the subject and controls operation of the positioning apparatus when the eyes of the subject are at a desired position or elevation.

To acquire an image of an object or subject's head, the system operator first enters object or subject specific information into system 100 utilizing input apparatus or keyboard 153 and display 151. The object or subject may be placed on positioning apparatus 1101.

An infant subject may be supported by an adult. The infant's head is not restrained and may move in motion having pivotal, rotational and translation components. When the adult and infant are in position the system clinician actuates system 100 to capture and simultaneously record multiple simultaneous images of the subject's head. Within a very short time a digital reconstructed three-dimensional representation of the entirety of the subject's head is constructed from the captured images and is viewable on display 151.

Once processed, the image data may be viewed in a variety of formats that include point cloud, wire frame, surface, and texture. As the name implies, the image presented as a point cloud consists of hundreds of thousands of independent single points of data. A wire frame, sometimes referred to as a polygon or triangulated mesh, connects three individual data points into a single polygon with each data point being referred to as a vertex. A wire frame is the first step in viewing the individual data points as one continuous connected 'surface'. Once connected as a series of polygons, mathematical algorithms are applied to convert the faceted, polygonized surface into a smooth continuous surface upon which more complex measurements and mathematical analyses can be performed. While point cloud, wire frame and surface rendering are the most common methods for viewing digital data, it is also possible to obtain texture information which is seamlessly overlaid on the model. Texture data is overlaid onto the digital image to ensure proper patient identification.

Display 151 may be advantageously utilized for a number of different uses. Illustratively, display 151 may provide video or video/audio programming that are likely to assist in having the subject position his/her head in a desired direction relative to structure 102.

Operation of system 100 may be substantially completely automatic such that once a subject enters system 100, the subject is automatically positioned to a desired position relative to structure 102 and when the subject is positioned at the desired position, the groups of image capturing apparatus 101a, 101b, 101c, 101d, 101e are automatically operated to capture a three-dimensional image or images of the subject.

Figure 12:
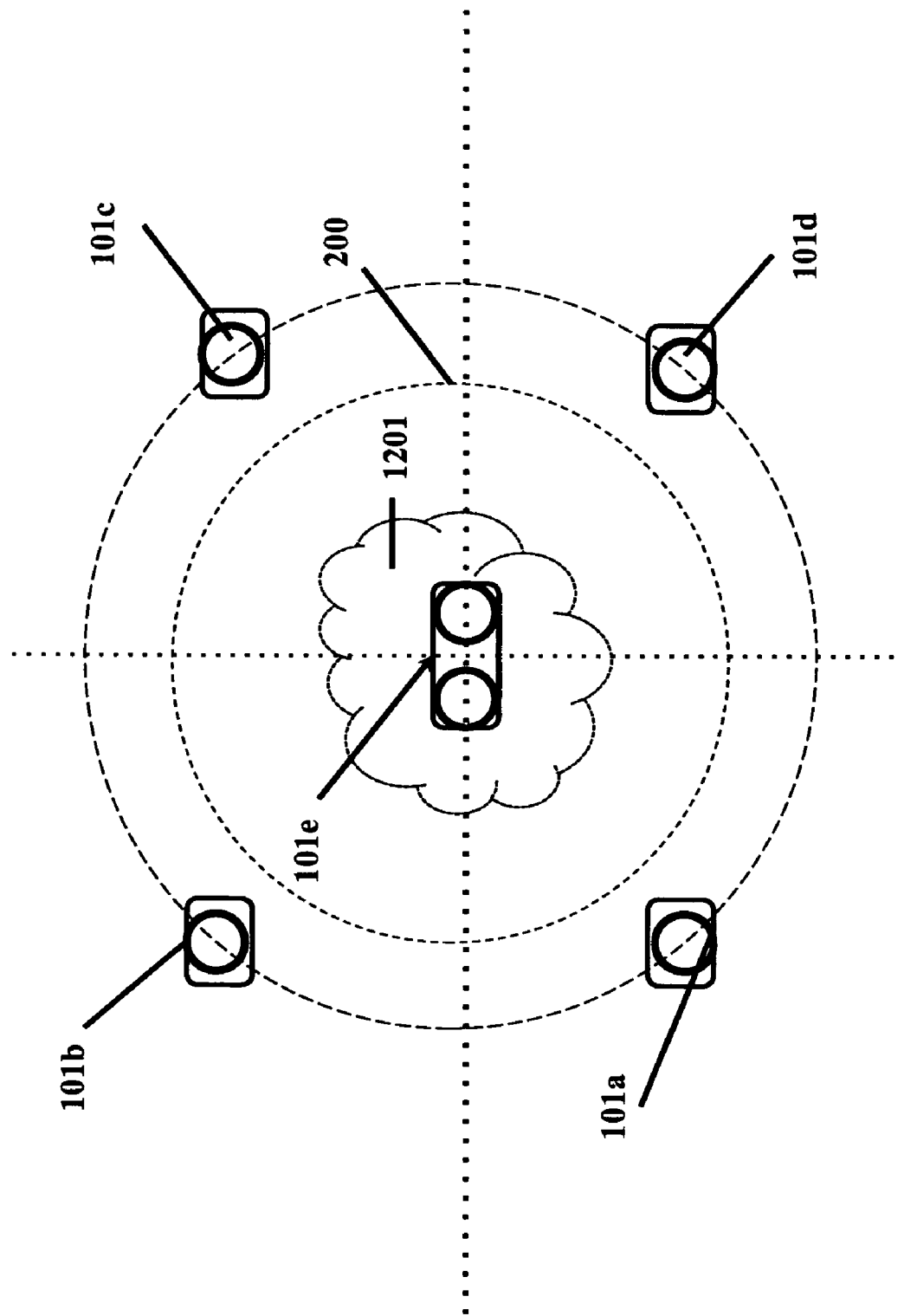
FIG. 12 is a top view schematic representation of the image capture system of FIG. 1.
Figure 13:
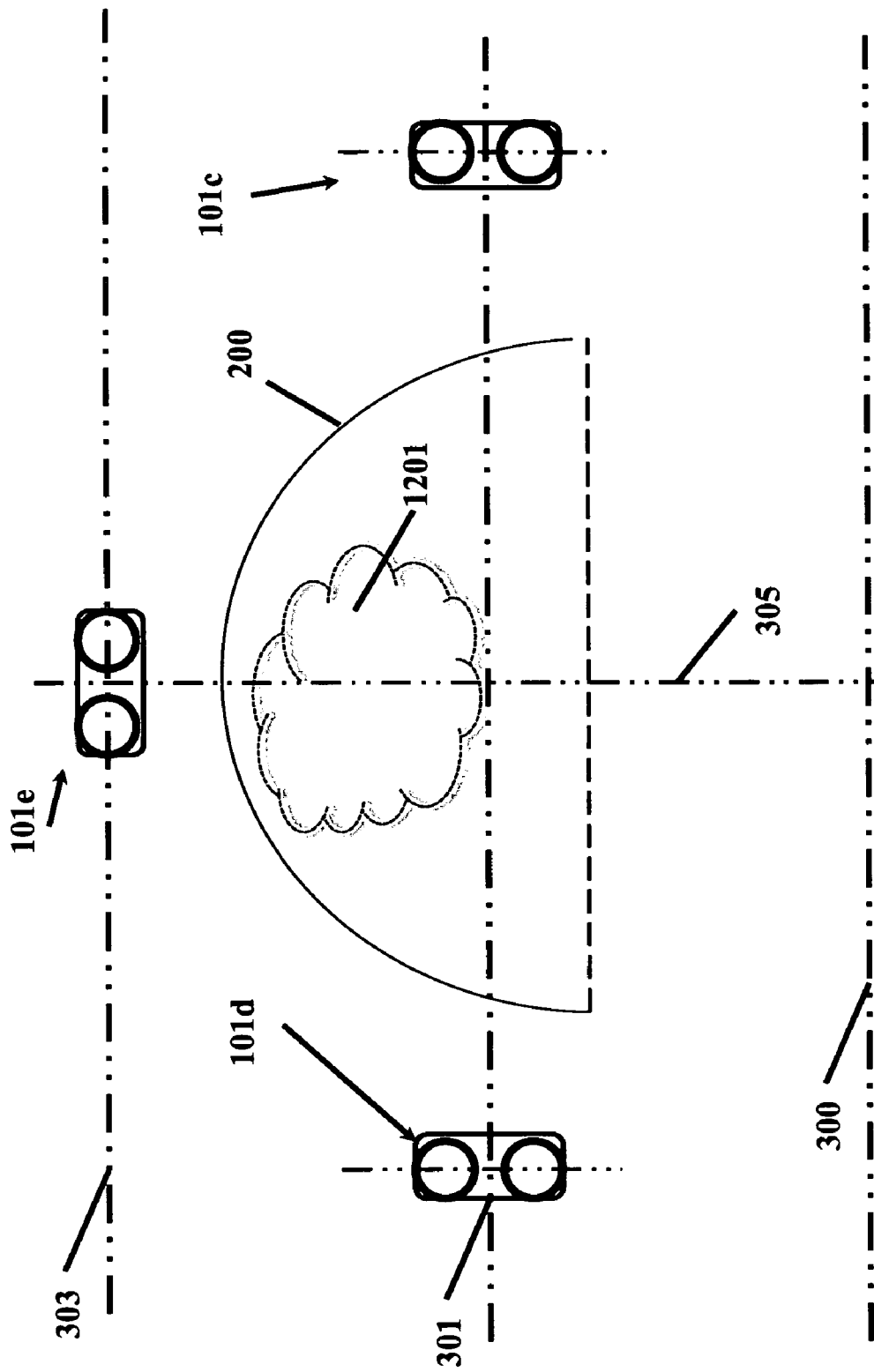
FIG. 13 is a side view schematic representation of the image capture system of FIG. 1.

Turning now to FIGS. 12 and 13, the relationships of the groups of image capturing apparatus 101a, 101b, 101c, 101d, 101e is shown. The object or subject 1201 that is to be digitally captured is positioned between planes 301 and 303 so that it is surrounded by the groups of image capturing apparatus 101a, 101b, 101c, 101d, 101e. The groups of image capturing apparatus 101a, 101b, 101c, 101d, 101e define a volumetric spatial region 200 within which three-dimensional images are captured.

Figure 14:
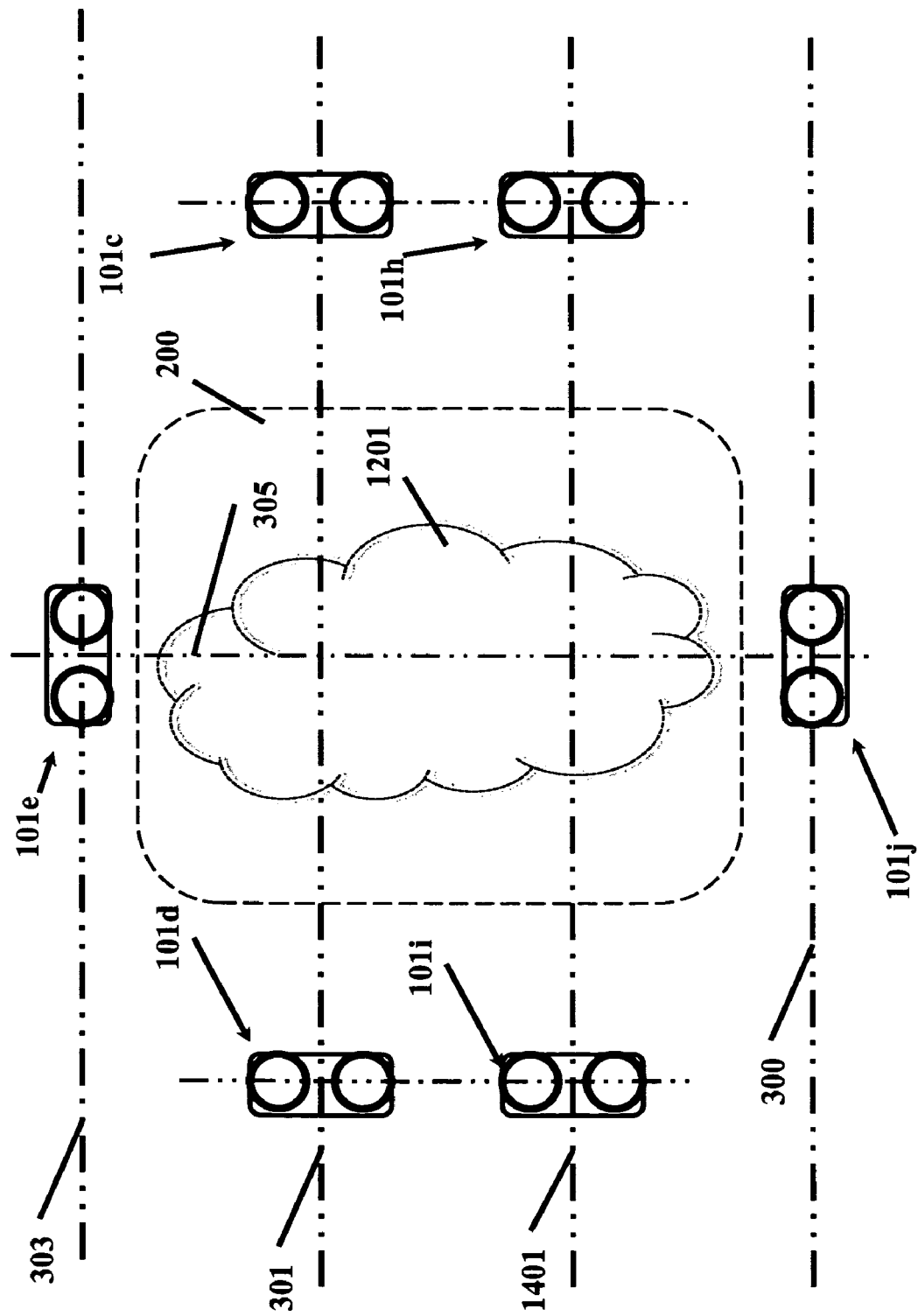
FIG. 14 is a side view schematic representation of a second embodiment of an image capture system in accordance with the principles of the invention.

In another embodiment of the invention, shown schematically in FIG. 14, an additional group of image capturing devices 101f, 101g, 101h, 101i are positioned in an additional plane 1401 and a further group of image capturing devices 101j is place in plane 300. Group 101f and 101g are not visible in FIG. 14, but are positioned below groups 101a, 101b, respectively. By providing additional image capturing devices in additional planes, high accuracy three-dimensional surface images may be obtained over larger objects or subjects 200. By way of non-limiting example, such an arrangement may capture full head and body images of a subject. It will be appreciated by those skilled in the art that the support structure of FIGS. 1 through 6 may be expanded to additionally provide fixed support to the additional group of image capturing devises 1301a, 1301b, 1301c, 1301d and further group of image capturing devices 1401f.

Turning back to the embodiment of system 100 shown in FIGS. 1-6, the surfaces of structure 102 are painted or otherwise treated to provide low reflectivity. The low reflectivity surfaces reduce reflection induced errors in the images captured by the various groups of image capturing devices.

The invention has been described in terms of specific embodiments. It will be appreciated by those skilled in the art that various changes and modifications may be made to the embodiments without departing from the scope of the invention. It is not intended that the invention be limited to the embodiments shown and described. It is intended that the invention include all foreseeable modifications to the embodiments shown and described. It is intended that the invention be limited in scope only by the claims appended hereto.

What is claimed is:

1. Apparatus to capture three-dimensional images of a subject's head, said apparatus comprising:
   a plurality of image capturing device groups, each of said groups comprising a plurality of image-capturing devices;
   a single support structure supporting said plurality of image capturing device groups in predetermined relationship to each other;
   said predetermined relationship defining a space;
   said support structure supporting said plurality of image capturing device groups in positions such that each said group is positioned to capture a group of first images of a corresponding surface portion of said subject's head disposed within said space, each said group of first images captured by the corresponding each of said image capturing device groups capturing a substantially different surface portion of said subject's head disposed within said space, each said group being disposed on said support structure such that the totality of the surface of said subject's head within said space is captured.

2. Apparatus in accordance with claim 1, wherein:
said support structure carries said plurality of image capturing device groups disposed in predetermined relationships to a plurality of planes.

3. Apparatus in accordance with claim 2, wherein:
said support structure carries at least a first one of said image capturing device groups disposed in a first predetermined relationship to a first plane and others of said image capturing device groups disposed in a second predetermined relationship to a second plane.

4. Apparatus in accordance with claim 3, wherein:
said first plane is parallel to and spaced apart from said second plane.

5. Apparatus in accordance with claim 4, wherein:
each of said image capturing device groups comprises a plurality of digital image capturing devices.

6. Apparatus in accordance with claim 5 wherein:
each of said digital image capturing devices comprises a digital camera.

7. Apparatus in accordance with claim 6, wherein:
each of said image capturing device groups comprises a projector.

8. Apparatus in accordance with claim 2, wherein:
said support structure carries at least a first one of said image capturing device groups disposed in a first predetermined relationship to a first plane and carries others of said image capturing device groups disposed in a second predetermined relationship to a second plane, each of said others of said image capturing device groups being disposed on said support structure equidistant from an imaginary axis extending perpendicular to said first and second planes through said at least a first one of said image capturing device groups.

9. Apparatus in accordance with claim 8, wherein:
said support structure comprises an arcuate portion carrying said others of said image capturing device groups.

10. Apparatus in accordance with claim 1, wherein:
said support structure carries said plurality of image capturing device groups disposed in predetermined relationships to first, second and third planes, such that said support structure carries at least a first one of said image capturing device groups in a first predetermined relationship to said first plane, carries at least second image capturing device groups in a second predetermined relationship to said second plane, and carries at least a third image capturing device group in a third predetermined relationship to said third plane.

11. Apparatus in accordance with claim 10, wherein:
said first, second and third planes are parallel.

12. Apparatus in accordance with claim 11, wherein:
said first and third planes are on opposite sides of said second plane.

13. Apparatus in accordance with claim 1, wherein:
said support structure comprises a first rigid substantially arcuate portion carrying a first portion of said image capturing device groups in a first predetermined spatial relationship, said support structure supporting each of said image capturing device groups in a predetermined alignment to a horizontal plane.

14. Apparatus in accordance with claim 13, comprising:
a plurality of vertical support structures, each supporting said first rigid substantially arcuate portion at a predetermined uniform height.

15. Apparatus in accordance with claim 14, wherein:
at least one of said vertical support structures extends above said first rigid structure and supports a second rigid structure portion substantially disposed in a second horizontal plane having a predetermined relationship to said first plane; and
said second rigid structure portion supports a second portion of said image capturing device groups in a predetermined fixed relationship above said first portion of said image capturing device groups.

16. Apparatus in accordance with claim 1, wherein:
said support structure comprises a plurality of rigid support elements rigidly coupled to each other.

17. Apparatus in accordance with claim 1, wherein:
said support structure comprises low-reflectivity surfaces.

18. Apparatus to capture three-dimensional images of a subject's head, said apparatus comprising:
a plurality of image capturing device modules, each of said modules comprising a plurality of image-capturing devices;
a rigid support structure rigidly supporting each of said image capturing device modules in predetermined relationship to each other such that one module of said modules is disposed in a first horizontal plane centered on a vertical axis and the remaining modules of said plurality image capturing device modules are disposed along the circumference of a circle in a second plane parallel to said first plane and centered on said vertical axis, said subject's head being disposed in a predetermined position with respect to said vertical axis and said second plane.

19. Apparatus in accordance with claim 18, wherein:
each of said remaining modules is spaced equidistant from each other.

20. Apparatus in accordance with claim 18, wherein:
said first horizontal plane is disposed a first predetermined distance above said second horizontal plane.

21. Apparatus in accordance with claim 20, wherein:
said second horizontal plane is disposed a second predetermined distance above ground.

22. Apparatus in accordance with claim 18, comprising:
subject positioning apparatus disposed within said rigid support structure in alignment with said axis.

23. Apparatus in accordance with claim 22, wherein:
said subject positioning apparatus comprises a vertically displaceable stool.

24. Apparatus in accordance with claim 23, wherein:
said rigid support apparatus comprises an opening for ingress and egress to said stool.

25. Apparatus to capture three-dimensional images of a subject's head, said apparatus comprising:
a plurality of image capturing device modules, each of said modules comprising a plurality of image-capturing devices;
a rigid support structure rigidly supporting each of said image capturing device modules in predetermined relationship to each other such that one module of said modules is disposed in a first horizontal plane centered on a vertical axis and the remaining modules of said plurality image capturing device modules are disposed along the circumference of a circle in a second plane parallel to said first plane and centered on said vertical axis, said subject's head being disposed in a predetermined position with respect to said vertical axis and said second plane;
said rigid support structure comprising first, second and third vertical supports, said first, second and third vertical supports being spaced along said circumference such that said first and second supports are spaced apart by the same circumferential distance as said second and third supports;
said rigid support structure comprising first, second, third and fourth arcuate support members; said first arcuate support member being rigidly coupled to said first vertical support; said second arcuate support member being rigidly coupled to said first and said second vertical supports; said third arcuate support member being rigidly coupled to said second and said third vertical supports; said fourth arcuate support member being rigidly coupled to said third vertical support;
said remaining modules comprising a first module supported on said first arcuate member, a second module supported on said second arcuate member; a third module supported on said third arcuate member; and a fourth module supported on said fourth arcuate member.

26. Apparatus in accordance with claim 25, wherein:
said first and said fourth arcuate members each have an unsupported end spaced apart from each other to provide an opening in said structure for ingress and egress.

27. Apparatus in accordance with claim 25, wherein:
said second vertical support extends above said second and third arcuate members and is rigidly coupled to a horizontal member, said horizontal member supporting said one module.

28. Apparatus in accordance with claim 27, wherein:
said second vertical support comprises an arcuate portion rigidly coupled to said horizontal member.

29. Apparatus in accordance with claim 28, comprising:
a display disposed within said second vertical support.

30. Apparatus to capture three-dimensional images of a subject's head, said apparatus comprising:
a plurality of image capturing modules;
each of said modules comprising a plurality of image-capturing devices;
a single support structure supporting said plurality of image capturing modules in predetermined relationship to each other;
said predetermined relationship defining a space;
said support structure supporting said plurality of image capturing modules in positions such that each said module is positioned to capture a group of first images of a corresponding surface portion of said subject's head disposed within said space, each said group of first images captured by the corresponding each said module capturing a substantially different surface portion of said subject's head disposed within said space, each said module being disposed on said structure such that first images of the totality of the surface of said subject's head within said space is captured.

31. Apparatus in accordance with claim 30, wherein:
said support structure carries said plurality of modules disposed in predetermined relationships to a plurality of planes.

32. Apparatus in accordance with claim 31, wherein:
said support structure carries at least a first one of said modules disposed in a first predetermined relationship to a first plane and others of said modules disposed in a second predetermined relationship to a second plane.

33. Apparatus in accordance with claim 32, wherein:
said first plane is parallel to and spaced apart from said second plane.

34. Apparatus in accordance with claim 33, wherein:
each of said modules comprises a plurality of digital image capturing devices.

35. Apparatus in accordance with claim 34, wherein:
each of said modules comprises a digital camera.

36. Apparatus in accordance with claim 35, wherein:
each of said modules comprises a projector.

37. Apparatus in accordance with claim 31, wherein:
said support structure carries at least a first one of said modules disposed in a first predetermined relationship to a first plane and carries others of said modules disposed in a second predetermined relationship to a second plane, each of said others of said modules being disposed on said support structure equidistant from an imaginary axis extending perpendicular to said first and second planes through said at least a first one of said modules.

38. Apparatus in accordance with claim 37, wherein:
said support structure comprises an arcuate portion carrying said others of said modules.

39. Apparatus in accordance with claim 30, wherein:
said support structure carries said plurality of modules disposed in predetermined relationships to first, second and third planes, such that said support structure carries at least a first one of said modules in a first predetermined relationship to said first plane, carries at least a second group of said modules in a second predetermined relationship to said second plane, and carries at least a third group of said modules in a third predetermined relationship to said third plane.

40. Apparatus in accordance with claim 39, wherein:
said first, second and third planes are parallel.

41. Apparatus in accordance with claim 40, wherein:
said first and third planes are on opposite sides of said second plane.

42. Apparatus in accordance with claim 40, wherein:
said support structure comprises a plurality of first rigid arcuate portion carrying one group of said modules in a first predetermined spatial relationship, said rigid arcuate portion supporting each of said modules in a predetermined alignment to a first plane.

43. Apparatus in accordance with claim 42, comprising:
said rigid arcuate portion comprises a plurality of vertical support elements and a plurality of arcuate elements, said vertical support elements supporting said plurality of arcuate elements at a predetermined uniform distance from a second plane.

44. Apparatus in accordance with claim 43, comprising:
a second rigid structure portion substantially disposed in a third plane having a predetermined relationship to said first plane; and
said second rigid structure portion supporting a second group of said modules in a predetermined fixed relationship to said one group of modules.

45. Apparatus in accordance with claim 30, wherein:
said support structure comprising a plurality of rigid support elements rigidly coupled to each other.

46. Apparatus in accordance with claim 30, wherein:
said support structure comprises low-reflectivity surfaces.

47. Apparatus to capture three-dimensional images of a subject's head, said apparatus comprising:
a plurality of image capturing device modules, each of said modules comprising a plurality of image-capturing devices;
a support structure supporting said image capturing device modules in predetermined relationship to each other such that at least one module of said modules is disposed in a first plane centered on an axis and others of said modules are disposed in a second plane parallel to said first plane and centered on said axis; and
apparatus automatically operating said plurality of image capturing device modules when said subject's head is disposed in a predetermined position with respect to said axis and said second plane.

48. Apparatus in accordance with claim 47, wherein:
said automatically operating apparatus comprises sensing apparatus to sense the position of said subject's head.

49. Apparatus in accordance with claim 48, wherein:
said automatically operating apparatus comprises subject displacing apparatus to automatically position said subject to said predetermined position.

50. Apparatus in accordance with claim 49, wherein:
said displacing apparatus comprises a vertically displaceable apparatus.

51. Apparatus in accordance with claim 49, wherein:
said vertically displaceable apparatus is electrically actuatable.

* * * * *